(12) United States Patent
Liu

(10) Patent No.: US 10,160,778 B2
(45) Date of Patent: Dec. 25, 2018

(54) PYRIMIDINE PHOSPHONIC ACID ESTERS

(71) Applicant: Concert Pharmaceuticals, Inc., Lexington, MA (US)

(72) Inventor: Julie F. Liu, Lexington, MA (US)

(73) Assignee: Concert Pharmaceuticals, Inc., Lexington, MA (US)

( * ) Notice: Subject to any disclaimer, the term of this patent is extended or adjusted under 35 U.S.C. 154(b) by 0 days.

(21) Appl. No.: 15/522,692

(22) PCT Filed: Oct. 27, 2015

(86) PCT No.: PCT/US2015/057630
§ 371 (c)(1),
(2) Date: Apr. 27, 2017

(87) PCT Pub. No.: WO2016/069630
PCT Pub. Date: May 6, 2016

(65) Prior Publication Data
US 2017/0334937 A1    Nov. 23, 2017

Related U.S. Application Data

(60) Provisional application No. 62/069,137, filed on Oct. 27, 2014.

(51) Int. Cl.
C07F 9/6512 (2006.01)
A61K 31/675 (2006.01)

(52) U.S. Cl.
CPC .......... *C07F 9/6512* (2013.01); *A61K 31/675* (2013.01); *C07F 9/65121* (2013.01)

(58) Field of Classification Search
CPC .................................................. C07F 9/6512
See application file for complete search history.

(56) References Cited

U.S. PATENT DOCUMENTS

| | | | |
|---|---|---|---|
| 5,650,510 A | 7/1997 | Webb, II et al. | |
| 6,221,335 B1 | 4/2001 | Foster | |
| 6,440,710 B1 | 8/2002 | Keinan et al. | |
| 6,603,008 B1 | 8/2003 | Ando et al. | |
| 6,716,825 B2 | 4/2004 | Hostetler et al. | |
| 7,517,990 B2 | 4/2009 | Ito et al. | |
| 8,642,577 B2 | 2/2014 | Almond et al. | |
| 2004/0067960 A1* | 4/2004 | Davis ................. | C07D 401/12 514/253.05 |
| 2007/0003516 A1 | 1/2007 | Almond et al. | |
| 2007/0082929 A1 | 4/2007 | Gant et al. | |
| 2007/0197533 A1* | 8/2007 | Zhou .................. | C07D 401/04 514/241 |
| 2007/0197695 A1 | 8/2007 | Potyen et al. | |
| 2008/0009462 A1* | 1/2008 | Hostetler ............ | C07F 9/65121 514/48 |
| 2008/0103122 A1 | 5/2008 | Veltri | |
| 2012/0058976 A1 | 3/2012 | Ware et al. | |
| 2012/0164104 A1 | 6/2012 | Lanier et al. | |
| 2013/0072458 A1 | 3/2013 | Painter et al. | |

FOREIGN PATENT DOCUMENTS

| | | |
|---|---|---|
| WO | WO 95/26325 | 10/1995 |
| WO | WO 2005/087788 | 9/2005 |
| WO | WO 2006/110655 | 10/2006 |
| WO | WO 2007/118651 | 10/2007 |
| WO | WO 2010/118286 | 10/2010 |
| WO | WO 2011/053812 | 5/2011 |
| WO | WO 2012/031045 | 3/2012 |

OTHER PUBLICATIONS

Painter et al. Antimicrob. Agents Chemother., vol. 56(5), p. 2726-2734 (Year: 2012).*

(Continued)

*Primary Examiner* — Emily A Bernhardt
(74) *Attorney, Agent, or Firm* — Fish & Richardson P.C.

(57) ABSTRACT

This invention relates to compounds of Formula (I):

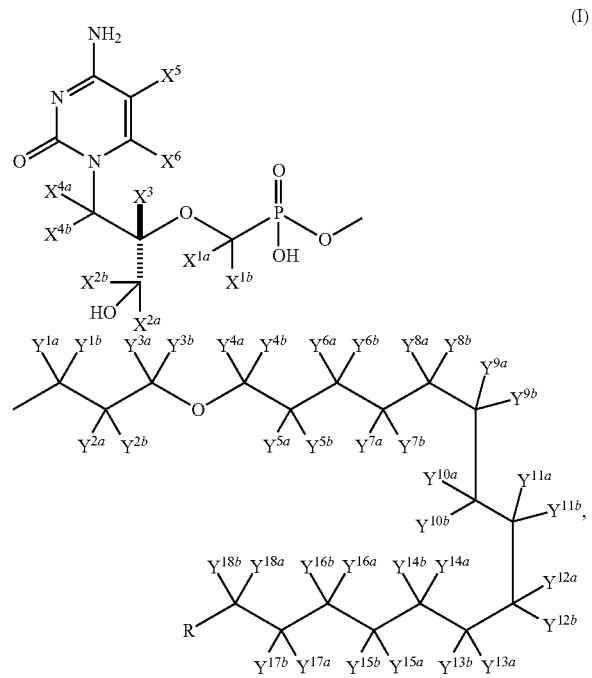

and pharmaceutically acceptable salts thereof, wherein $Y^{1a}$, $Y^{1b}$, $Y^{2a}$, $Y^{2b}$, $Y^{3a}$, and $Y^{3b}$ are each independently selected from hydrogen and deuterium, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$ are each deuterium, $X^{1a}$, $X^{1b}$, $X^{2a}$, $X^{2b}$, $X^{3}$, $X^{4a}$, $X^{4b}$, $X^{5}$, and $X^{6}$ are each independently selected from hydrogen and deuterium; and R is $CD_3$. This invention also provides compositions comprising a compound of this invention and the use of such compositions in methods of treating diseases and conditions that are beneficially treated by administering a viral DNA polymerase inhibitor.

19 Claims, No Drawings

(56) References Cited

OTHER PUBLICATIONS

International Preliminary Report on Patentability for International Application No. PCT/US2015/057630, dated May 11, 2017, 7 pages.

Baillie, "The Use of Stable Isotopes in Pharmacological Research," *Pharmacology Rev*, 1981, 33(2):81-132.

Bronson et al: "Synthesis and antiviral activity of the nucleotide analog (S)-1-[3-hydroxy-2-(phosphonylmethoxy)propyl]cystosine," Journal of Medicinal Chemistry, Jul. 1, 1989, 32(7):1457-1463.

Browne, "Stable Isotope Techniques in Early Drug Development: An Economic Evaluation," *J. Clin. Pharmacology*, 1998, 38: 213-20.

Cherrah et al., "Study of Deuterium Isotope Effects on Protein Binding by Gas Chromatography/Mass Spectrometry. Caffeine and Deuterated Isotopomers," *Biomed. and Environmental Mass Spectrometry*, 1987, 14: 653-57.

Dyck et al., "Effects of Deuterium Substitution on the Catabolism of ?-Phenylethylamine: An In Vivo Study," *J. Neurochemistry*, 1986, 46: 399-404.

Fisher et al., "The complexities inherent in attempts to decrease drug clearance by blocking sites of CYP-mediated metabolism," *Curr. Opin. Drug Discov. Dev.*, 2006, 9(1):101-109.

Foster, "Deuterium isotope effects in studies of drug metabolism," *Trends in Pharmaceutical Sciences*, 1984, 524-527.

Foster, "Deuterium Isotope Effects in the Metabolism of Drugs and Xenobiotics: Implications for Drug Design," *Adv. Drug Res.*, 1985, 14: 2-40.

Gouyette, "Synthesis of Deuterium-labelled Elliptinium and its Use in Metabolic Studies," *Biomed. and Environmental Mass Spectrometry*, 1988, 15: 243-47.

Haskins, "The Application of Stable Isotopes in Biomedical Research," *Biomed. Spectrometry*, 1982, 9(7):269-77.

Honma et al., "The Metabolism of Roxatidine Acetate Hydrochloride," *Drug Metab. Dispos*, 1987, 15(4): 551-559.

Hostetler, "Synthesis and Early Development of Hexadecyloxypropylcidofovir: An Oral Antipoxvirus Nucleoside Phosphonate," Viruses, Sep. 30, 2010, 2(10):2213-2225.

International Search Report for International Application No. PCT/US2015/057630, dated Dec. 9, 2015, 12 pages.

Kao et al: "Synthesis of anti-CVM RPR111423 labeled with carbon-14, deuterium and tritium," Synthesis and Applications of Isotopically Labelled Compounds, : vol. 7: Proceedings of the International Symposium, 7th Dresden, Jun. 18-22, 2000, Jan. 1, 2000, pp. 283-286.

Kern et al., "Enhanced Inhibition of Orthopoxvirus Replication In Vitro by Alkoxyalkyl Esters of Cidofovir and Cyclic Cidofovir," Antimicrobial Agents and Chemotherapy, Apr. 2002, 46(4):991-995.

Kushner et al. "Pharmacological uses and perspectives of heavy water and deuterated compounds," *Can. J. Physiol. Pharmacol.* 1999, 77: 79-88.

Pieniaszek et al., "Moricizine bioavailability via simultaneous, dual, stable isotope administrations: bioequivalence," *J. Clin. Pharmacology*, 1999, 39:817-25.

Tonn et al., "Simultaneous Analysis of Diphenhydramine and a Stable Isotope Analog ($^2$H10) Diphenhydramine Using Capillary Gas Chromatography with Mass Selective Detection in Biological Fluids from Chronically Instrumented Pregnant Ewes," *Biol. Mass Spectrometry*, 1993, 22:633-642.

Tung R: "The Development of Deuterium-Containing Drugs," Innovations in Pharmaceutical Technology, Samedan Ltd, GB, Mar. 1, 2010, 32:24-26, 28.

Wolen, "The Application of Stable Isotopes to Studies of Drug Bioavailability and Bioequivalence," *J. Clin. Pharmacology*, 1986, 26:419-424.

ClinicalTrials.gov' [online]. "A Multicenter, Open-label Study of CMX001 Treatment of Serious Diseases or Conditions Caused by dsDNA Viruses," ClinicalTrials.gov Identifier: NCT01143181, First Posted Jun. 14, 2010, [retreived on Jul. 20, 2018]. Retrieved from the Internet: URL<https://clinicaltrials.gov/ct2/show/NCT01143181?term=brincidofovir&draw=3&rank=14>, 6 pages.

ClinicalTrials.gov' [online]. "A Study of the Safety and Efficacy of CMX001 for the Prevention of Cytomegalovims (CMV) Infection in CMV-seropositive (R+) Hematopoietic Stem Cell Transplant Recipients," ClinicalTrials.gov Identifier: NCT01769170, First Posted Jan. 16, 2013, [retreived on Jul. 20, 2018]. Retrieved from the Internet: URL<https://clinicaltrials.gov/ct2/show/NCT01769170?term=brincidofovir&draw=4&rank=6>, 5 pages.

ClinicalTrials.gov' [online]. "An Open-Label, Multicenter Study of the Safety and Anti Viral Activity of Brincidofovir (BCV, CMX001) for Ebola Virus Disease (CMX)," ClinicalTrials.gov Identifier: NCT02271347, First Posted Oct. 22, 2014, [retreived on Jul. 20, 2018]. Retrieved from the Internet: URL<https://clinicaltrials.gov/ct2/show/NCT02271347?term=brincidofovir&draw=4&rank=3>, 4 pages.

ClinicalTrials.gov' [online]. "Phase III, Open-labeled, Multicenter Study of the Safety and Efficacy of Brincidofovir (CMX001) in the Treatment of Early Versus Late Adenovirus Infection (CMX001 Adv)," ClinicalTrials.gov Identifier: NCT02087306, First Posted Mar. 14, 2014, [retreived on Jul. 20, 2018]. Retrieved from the Internet: URL<https://clinicaltrials.gov/ct2/show/NCT02087306?term=brincidofovir&draw=2&rank=1>, 5 pages.

\* cited by examiner

PYRIMIDINE PHOSPHONIC ACID ESTERS

CLAIM FOR PRIORITY

This application is a § 371 National Stage Application of PCT/US2015/057630, filed Oct. 27, 2015, which claims the benefit of U.S. Provisional Application No. 62/069,137, filed Oct. 27, 2014. The entire contents of the foregoing are hereby incorporated by reference.

BACKGROUND OF THE INVENTION

Many current medicines suffer from poor absorption, distribution, metabolism and/or excretion (ADME) properties that prevent their wider use or limit their use in certain indications. Poor ADME properties are also a major reason for the failure of drug candidates in clinical trials. While formulation technologies and prodrug strategies can be employed in some cases to improve certain ADME properties, these approaches often fail to address the underlying ADME problems that exist for many drugs and drug candidates. One such problem is rapid metabolism that causes a number of drugs, which otherwise would be highly effective in treating a disease, to be cleared too rapidly from the body. A possible solution to rapid drug clearance is frequent or high dosing to attain a sufficiently high plasma level of drug. This, however, introduces a number of potential treatment problems such as poor patient compliance with the dosing regimen, side effects that become more acute with higher doses, and increased cost of treatment. A rapidly metabolized drug may also expose patients to undesirable toxic or reactive metabolites.

Another ADME limitation that affects many medicines is the formation of toxic or biologically reactive metabolites. As a result, some patients receiving the drug may experience toxicities, or the safe dosing of such drugs may be limited such that patients receive a suboptimal amount of the active agent. In certain cases, modifying dosing intervals or formulation approaches can help to reduce clinical adverse effects, but often the formation of such undesirable metabolites is intrinsic to the metabolism of the compound.

In some select cases, a metabolic inhibitor will be co-administered with a drug that is cleared too rapidly. Such is the case with the protease inhibitor class of drugs that are used to treat HIV infection. The FDA recommends that these drugs be co-dosed with ritonavir, an inhibitor of cytochrome P450 enzyme 3A4 (CYP3A4), the enzyme typically responsible for their metabolism (see Kempf, D. J. et al., Antimicrobial agents and chemotherapy, 1997, 41(3): 654-60). Ritonavir, however, causes adverse effects and adds to the pill burden for HIV patients who must already take a combination of different drugs. Similarly, the CYP2D6 inhibitor quinidine has been added to dextromethorphan for the purpose of reducing rapid CYP2D6 metabolism of dextromethorphan in a treatment of pseudobulbar affect. Quinidine, however, has unwanted side effects that greatly limit its use in potential combination therapy (see Wang, L et al., Clinical Pharmacology and Therapeutics, 1994, 56(6 Pt 1): 659-67; and FDA label for quinidine at www.accessdata.fda.gov).

In general, combining drugs with cytochrome P450 inhibitors is not a satisfactory strategy for decreasing drug clearance. The inhibition of a CYP enzyme's activity can affect the metabolism and clearance of other drugs metabolized by that same enzyme. CYP inhibition can cause other drugs to accumulate in the body to toxic levels.

A potentially attractive strategy for improving a drug's metabolic properties is deuterium modification. In this approach, one attempts to slow the CYP-mediated metabolism of a drug or to reduce the formation of undesirable metabolites by replacing one or more hydrogen atoms with deuterium atoms. Deuterium is a safe, stable, non-radioactive isotope of hydrogen. Compared to hydrogen, deuterium forms stronger bonds with carbon. In select cases, the increased bond strength imparted by deuterium can positively impact the ADME properties of a drug, creating the potential for improved drug efficacy, safety, and/or tolerability. At the same time, because the size and shape of deuterium are essentially identical to those of hydrogen, replacement of hydrogen by deuterium would not be expected to affect the biochemical potency and selectivity of the drug as compared to the original chemical entity that contains only hydrogen.

Over the past 35 years, the effects of deuterium substitution on the rate of metabolism have been reported for a very small percentage of approved drugs (see, e.g., Blake, M I et al, J Pharm Sci, 1975, 64:367-91; Foster, A B, Adv Drug Res 1985, 14:1-40 ("Foster"); Kushner, D J et al, Can J Physiol Pharmacol 1999, 79-88; Fisher, M B et al, Curr Opin Drug Discov Devel, 2006, 9:101-09 ("Fisher")). The results have been variable and unpredictable. For some compounds deuteration caused decreased metabolic clearance in vivo. For others, there was no change in metabolism. Still others demonstrated increased metabolic clearance. The variability in deuterium effects has also led experts to question or dismiss deuterium modification as a viable drug design strategy for inhibiting adverse metabolism (see Foster at p. 35 and Fisher at p. 101).

The effects of deuterium modification on a drug's metabolic properties are not predictable even when deuterium atoms are incorporated at known sites of metabolism. Only by actually preparing and testing a deuterated drug can one determine if and how the rate of metabolism will differ from that of its non-deuterated counterpart. See, for example, Fukuto et al. (J. Med. Chem. 1991, 34, 2871-76). Many drugs have multiple sites where metabolism is possible. The site(s) where deuterium substitution is required and the extent of deuteration necessary to see an effect on metabolism, if any, will be different for each drug.

SUMMARY OF THE INVENTION

This invention relates to novel pyrimidine phosphonic acid esters, and pharmaceutically acceptable salts thereof. This invention also provides compositions comprising a compound of this invention and the use of such compositions in methods of preventing and/or treating diseases and conditions that are beneficially prevented and/or treated by administering a viral DNA polymerase inhibitor.

Brincidofovir, also known as CMX001, cidofovir-HDP, hexadecyloxypropyl-cidofovir, and 3-(hexadecyloxy)propyl hydrogen ((((S)-1-(4-amino-2-oxopyrimidin-1 (2H)-yl)-3-hydroxypropan-2-yl)oxy)methyl)phosphonate, modulates the replication of double-stranded DNA (dsDNA) viruses.

Brincidofovir is currently in phase III clinical trials for the prevention of cytomegalovirus infection in CMV-seropositive hematopoietic stem cell transplant recipients and for the treatment of early versus late adenovirus infection. Phase II/III trials are also underway for the treatment of adult and pediatric patients with life-threatening or serious conditions caused by dsDNA viral infections for which no satisfactory alternate therapy is available (including immunocompromised patients). Early clinical development is under way for the treatment of smallpox infection. An emergency Investigational New Drug application has been filed in the United States for the treatment of Ebola virus infection.

In a phase II study for the prevention of cytomegalovirus infection, diarrhea was found to be a dose-limiting side effect of brincidofovir.

Despite the beneficial activities of brincidofovir, there is a continuing need for new compounds to treat the aforementioned diseases and conditions.

DETAILED DESCRIPTION OF THE INVENTION

Definitions

The term "treat" means decrease, suppress, attenuate, diminish, arrest, or stabilize the development or progression of a disease (e.g., a disease or disorder delineated herein), lessen the severity of the disease or improve the symptoms associated with the disease.

The term "prevent" includes both therapeutic and prophylactic treatment and means decrease, suppress, attenuate, diminish, arrest, or stabilize the development or progression of a disease (e.g., a disease or disorder delineated herein) in order to preclude the occurrence of the disease.

"Disease" means any condition or disorder that damages or interferes with the normal function of a cell, tissue, or organ.

"The term "alkyl" refers to a monovalent saturated hydrocarbon group. $C_1$-$C_6$ alkyl is an alkyl having from 1 to 6 carbon atoms. An alkyl may be linear or branched. Examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl.

Unless otherwise specified, "alkylene" by itself or as part of another substituent refers to a saturated straight-chain or branched divalent group having the stated number of carbon atoms and derived from the removal of two hydrogen atoms from the corresponding alkane. Examples of straight chained and branched alkylene groups include —$CH_2$— (methylene), —$CH_2$—$CH_2$— (ethylene), —$CH_2$—$CH_2$—$CH_2$— (propylene), —$C(CH_3)_2$—, —$CH_2$—$CH(CH_3)$—, —$CH_2$—$CH_2$—$CH_2$—$CH_2$—, —$CH_2$—$CH_2$—$CH_2$—$CH_2$—$CH_2$— (pentylene), —$CH_2$—$CH(CH_3)$—$CH_2$—, and —$CH_2$—$C(CH_3)_2$—$CH_2$—.

The term "heteroaryl" refers to a monovalent aromatic monocyclic ring system wherein at least one ring atoms is a heteroatom independently selected from the group consisting of O, N and S. The term 5-membered heteroaryl refers to a heteroaryl wherein the number of ring atoms is 5. Examples of 5-membered heteroaryl groups include pyrrolyl, pyrazolyl, oxazolyl, isoxazolyl, thiazolyl, isothiazolyl, oxadiazolyl, thiadiazolyl, furazanyl, imidazolinyl, and triazolyl.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. In one embodiment, the alkyl moiety of the heteroarylalkyl is ($C_1$-$C_6$) alkyl and the heteroaryl moiety is a 5-14-membered heteroaryl. In a more specific embodiment, the alkyl moiety is ($C_1$-$C_3$) alkyl and the heteroaryl moiety is a 5-10 membered heteroaryl.

It will be recognized that some variation of natural isotopic abundance occurs in a synthesized compound depending upon the origin of chemical materials used in the synthesis. Thus, a preparation of brincidofovir will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

The term "isotopic enrichment factor" as used herein means the ratio between the isotopic abundance and the natural abundance of a specified isotope.

In other embodiments, a compound of this invention has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5%) deuterium incorporation).

The term "isotopologue" refers to a species in which the chemical structure differs from a specific compound of this invention only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that a compound represented by a particular chemical structure containing indicated deuterium atoms, will also contain lesser amounts of isotopologues having hydrogen atoms at one or more of the designated deuterium positions in that structure. The relative amount of such isotopologues in a compound of this invention will depend upon a number of factors including the isotopic purity of deuterated reagents used to make the compound and the efficiency of incorporation of deuterium in the various synthesis steps used to prepare the compound. However, as set forth above the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of the compounds of the invention.

A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The pharmaceutically acceptable salt may also be a salt of a compound of the present invention having an acidic functional group, such as a carboxylic acid or a phosphonic acid functional group, and a base. Exemplary bases include, but are not limited to, hydroxide of alkali metals including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

The compounds of the present invention (e.g., compounds of Formula I), may contain an asymmetric carbon atom, for example, as the result of deuterium substitution or otherwise. As such, compounds of this invention can exist as either individual enantiomers, or mixtures of the two enantiomers. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, preferably less than 10% of other stereoisomers, more preferably less than 5% of other stereoisomers and most preferably less than 2% of other stereoisomers are present. Methods of obtaining or synthesizing an individual enantiomer for a given compound are known in the art and may be applied as practicable to final compounds or to starting material or intermediates.

Unless otherwise indicated, when a disclosed compound is named or depicted by a structure without specifying the stereochemistry and has one or more chiral centers, it is understood to represent all possible stereoisomers of the compound.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, preventing and/or treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

Throughout this specification, a variable may be referred to generally (e.g., "each Y") or may be referred to specifically (e.g., $Y^{1a}$, $Y^{1b}$, $Y^{2a}$, etc.). Unless otherwise indicated, when a variable is referred to generally, it is meant to include all specific embodiments of that particular variable.

Therapeutic Compounds

The present invention provides a compound of Formula A:

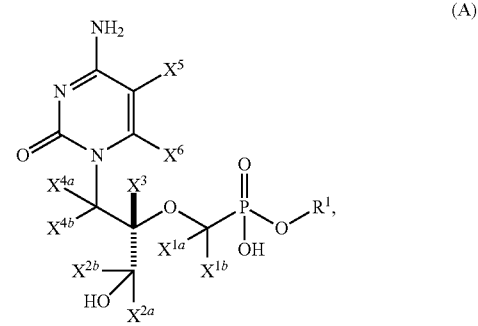

(A)

and pharmaceutically acceptable salts thereof, $R^1$ is selected from hydrogen and

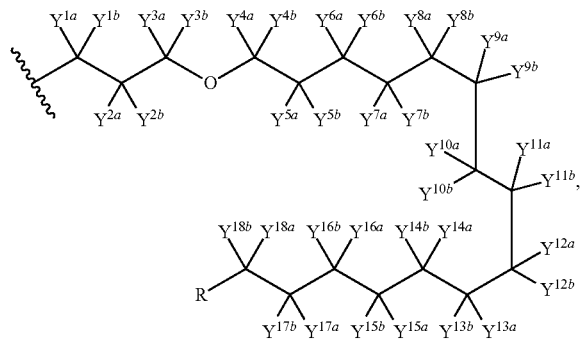

wherein $Y^{1a}$, $Y^{1b}$, $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$ are each independently selected from hydrogen and deuterium; $X^{1a}$, $X^{1b}$, $X^{2a}$, $X^{2b}$, $X^3$, $X^{4a}$, $X^{4b}$, $X^5$, and $X^6$ are each independently selected from hydrogen and deuterium; and R is selected from $CH_3$, $CH_2D$, $CHD_2$, and $CD_3$; provided that when $R^1$ is hydrogen, at least one of $X^{1a}$, $X^{1b}$, $X^{2a}$, $X^{2b}$, $X^3$, $X^{4a}$, $X^4$, $X^5$, and $X^6$ is deuterium; and when $Y^{1a}$, $Y^{1b}$, $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, $Y^{18b}$, $X^{1a}$, $X^{1b}$, $X^{2a}$, $X^{2b}$, $X^3$, $X^{4a}$, $X^{4b}$, $X^5$, and $X^6$ are all hydrogen, then R comprises at least one deuterium.

In certain embodiments of Formula A, $X^{1a}$ and $X^{1b}$ are the same. In one aspect of these embodiments, $X^{1a}$ and $X^{1b}$ are hydrogen. In an alternate aspect of these embodiments, $X^{1a}$ and $X^{1b}$ are deuterium.

In certain embodiments of Formula A, $X^{2a}$ and $X^{2b}$ are the same. In one aspect of these embodiments, $X^{2a}$ and $X^{2b}$ are hydrogen. In an alternate aspect of these embodiments, $X^{2a}$ and $X^{2b}$ are deuterium.

In certain embodiments of Formula A, $X^3$ is hydrogen. In an alternate aspect of these embodiments, $X^3$ is deuterium.

In certain embodiments of Formula A, $X^{4a}$ and $X^{4b}$ are the same. In one aspect of these embodiments, $X^{4a}$ and $X^{4b}$ are hydrogen. In an alternate aspect of these embodiments, $X^{4a}$ and $X^{4b}$ are deuterium.

In certain embodiments of Formula A, $X^5$ and $X^6$ are the same. In one aspect of these embodiments, $X^5$ and $X^6$ are hydrogen. In an alternate aspect of these embodiments, $X^5$ and $X^6$ are deuterium.

In certain embodiments of Formula A, $X^{1a}$ and $X^{1b}$ are the same; $X^{2a}$ and $X^{2b}$ are the same; $X^{4a}$ and $X^{4b}$ are the same; and $X^5$ and $X^6$ are the same.

In certain embodiments of Formula A, R is selected from $CH_3$, and $CD_3$. In some aspects of these embodiments, R is $CD_3$. In other aspects of these embodiments, R is $CH_3$.

In some embodiments, $R^1$ is

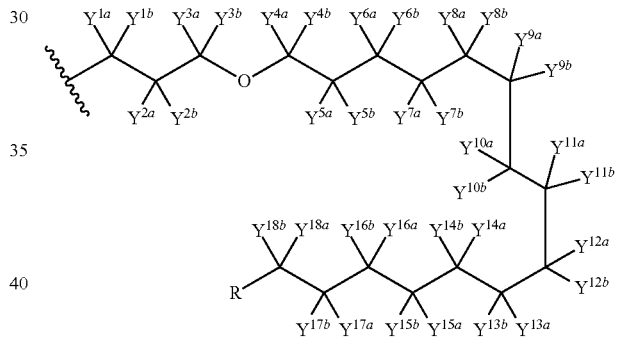

and the compound is a compound of Formula I:

(I)

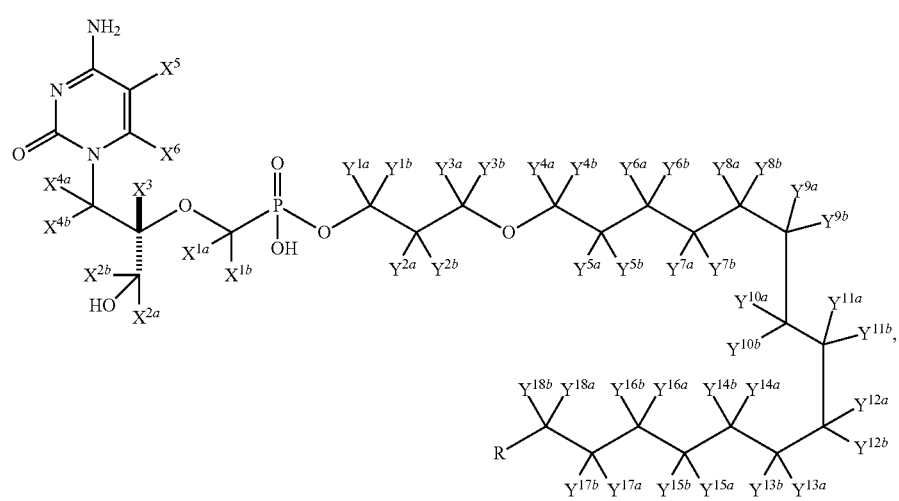

or a pharmaceutically acceptable salt thereof.

In some embodiments of Formula I, $Y^{1a}$ and $Y^{1b}$ are the same. In some aspects of these embodiments, $Y^{1a}$ and $Y^{1b}$ are both deuterium. In some aspects of these embodiments, $Y^{1a}$ and $Y^{1b}$ are both hydrogen.

In some embodiments of Formula I, $Y^{2a}$ and $Y^{2b}$ are the same. In some aspects of these embodiments, $Y^{2a}$ and $Y^{2b}$ are both deuterium. In some aspects of these embodiments, $Y^{2a}$ and $Y^{2b}$ are both hydrogen.

In some embodiments of Formula I, $Y^{3a}$ and $Y^{3b}$ are the same. In some aspects of these embodiments, $Y^{3a}$ and $Y^{3b}$ are both deuterium. In some aspects of these embodiments, $Y^{3a}$ and $Y^{3b}$ are both hydrogen.

In some embodiments of Formula I, $Y^{4a}$ and $Y^{4b}$ are the same. In some aspects of these embodiments, $Y^{4a}$ and $Y^{4b}$ are both deuterium. In some aspects of these embodiments, $Y^{4a}$ and $Y^{4b}$ are both hydrogen.

In some embodiments of Formula I, $Y^{5a}$ and $Y^{5b}$ are the same. In some aspects of these embodiments, $Y^{5a}$ and $Y^{5b}$ are both deuterium. In some aspects of these embodiments, $Y^{5a}$ and $Y^{5b}$ are both hydrogen.

In some embodiments of Formula I, $Y^{6a}$ and $Y^{6b}$ are the same. In some aspects of these embodiments, $Y^{6a}$ and $Y^{6b}$ are both deuterium. In some aspects of these embodiments, $Y^{6a}$ and $Y^{6b}$ are both hydrogen.

In some embodiments of Formula I, $Y^{7a}$ and $Y^{7b}$ are the same. In some aspects of these embodiments, $Y^{7a}$ and $Y^{7b}$ are both deuterium. In some aspects of these embodiments, $Y^{7a}$ and $Y^{7b}$ are both hydrogen.

In some embodiments of Formula I, $Y^{8a}$ and $Y^{8b}$ are the same. In some aspects of these embodiments, $Y^{8a}$ and $Y^{8b}$ are both deuterium. In some aspects of these embodiments, $Y^{8a}$ and $Y^{8b}$ are both hydrogen.

In some embodiments of Formula I, $Y^{9a}$ and $Y^{9b}$ are the same. In some aspects of these embodiments, $Y^{9a}$ and $Y^{9b}$ are both deuterium. In some aspects of these embodiments, $Y^{9a}$ and $Y^{9b}$ are both hydrogen.

In some embodiments of Formula I, $Y^{10a}$ and $Y^{10b}$ are the same. In some aspects of these embodiments, $Y^{10a}$ and $Y^{10b}$ are both deuterium. In some aspects of these embodiments, $Y^{10a}$ and $Y^{10b}$ are both hydrogen.

In some embodiments of Formula I, $Y^{11a}$ and $Y^{11b}$ are the same. In some aspects of these embodiments, $Y^{11a}$ and $Y^{11b}$ are both deuterium. In some aspects of these embodiments, $Y^{11a}$ and $Y^{11b}$ are both hydrogen.

In some embodiments of Formula I, $Y^{12a}$ and $Y^{12b}$ are the same. In some aspects of these embodiments, $Y^{12a}$ and $Y^{12b}$ are both deuterium. In some aspects of these embodiments, $Y^{12a}$ and $Y^{12b}$ are both hydrogen.

In some embodiments of Formula I, $Y^{13a}$ and $Y^{13b}$ are the same. In some aspects of these embodiments, $Y^{13a}$ and $Y^{13b}$ are both deuterium. In some aspects of these embodiments, $Y^{13a}$ and $Y^{13b}$ are both hydrogen.

In some embodiments of Formula I, $Y^{14a}$ and $Y^{14b}$ are the same. In some aspects of these embodiments, $Y^{14a}$ and $Y^{14b}$ are both deuterium. In some aspects of these embodiments, $Y^{14a}$ and $Y^{14b}$ are both hydrogen.

In some embodiments of Formula I, $Y^{15a}$ and $Y^{15b}$ are the same. In some aspects of these embodiments, $Y^{15a}$ and $Y^{15b}$ are both deuterium. In some aspects of these embodiments, $Y^{15a}$ and $Y^{15b}$ are both hydrogen.

In some embodiments of Formula I, $Y^{16a}$ and $Y^{16b}$ are the same. In some aspects of these embodiments, $Y^{16a}$ and $Y^{16b}$ are both deuterium. In some aspects of these embodiments, $Y^{16a}$ and $Y^{16b}$ are both hydrogen.

In some embodiments of Formula I, $Y^{17a}$ and $Y^{17b}$ are the same. In some aspects of these embodiments, $Y^{17a}$ and $Y^{17b}$ are both deuterium. In some aspects of these embodiments, $Y^{17a}$ and $Y^{17b}$ are both hydrogen.

In some embodiments of Formula I, $Y^{18a}$ and $Y^{18b}$ are the same. In some aspects of these embodiments, $Y^{18a}$ and $Y^{18b}$ are both deuterium. In some aspects of these embodiments, $Y^{18a}$ and $Y^{18b}$ are both hydrogen.

In some embodiments of Formula I, $Y^{1a}$, $Y^{1b}$, $Y^{2a}$, $Y^{2b}$, $Y^{3a}$, and $Y^{3b}$ are all the same. In some aspects of these embodiments, $Y^{1a}$, $Y^{1b}$, $Y^{2a}$, $Y^{2b}$, $Y^{3a}$ and $Y^{3b}$ are all deuterium, and R is $CD_3$. In some embodiments, $Y^{1a}$, $Y^{1b}$, $Y^{2a}$, $Y^{2b}$, $Y^{3a}$, and $Y^{3b}$ are all deuterium, and R is $CH_3$.

In some embodiments of Formula I, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$, are all the same. In some aspects of these embodiments, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$, are all deuterium, and R is $CD_3$. In some embodiments, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$ are all deuterium, and R is $CH_3$.

In some embodiments of Formula I, $Y^{1a}$, $Y^{1b}$, $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$, are all the same. In some aspects of these embodiments, $Y^{1a}$, $Y^{1b}$, $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$, are all deuterium, and R is $CD_3$. In some embodiments, $Y^{1a}$, $Y^{1b}$, $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$, are all deuterium, and R is $CH_3$.

In some embodiments of Formula I, $Y^{1a}$, $Y^{1b}$, $Y^{2a}$, $Y^{2b}$, $Y^{3a}$, and $Y^{3b}$ are all the same $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$ are all the same.

In certain embodiments of Formula I, R is selected from $CH_3$, and $CD_3$. In some aspects of these embodiments, R is $CD_3$. In other aspects of these embodiments, R is $CH_3$.

Embodiments of Formula I relating to one or more of $X^{1a}$, $X^{1b}$, $X^{2a}$, $X^{2b}$, $X^3$, $X^{4a}$, $X^{4b}$, $X^5$, and $X^6$, and specific aspects thereof are the same as those set forth above for Formula A.

In some embodiments of Formula I, $X^{1a}$ and $X^{1b}$ are the same; $X^{2a}$ and $X^{2b}$ are the same; $X^{4a}$ and $X^{4b}$ are the same; and $X^5$ and $X^6$ are the same; $Y^{1a}$, $Y^{1b}$, $Y^{2a}$, $Y^{2b}$, $Y^{3a}$, and $Y^{3b}$ are all the same; $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, and $Y^{18a}$, and $Y^{18b}$ are all the same, and the compound is selected from any one of the compounds set forth in Table 1 (below):

TABLE 1

Exemplary Embodiments of Formula I

| Compound # | $X^{1a}/X^{1b}$ | $X^{2a}/X^{2b}$ | $X^3$ | $X^{4a}/X^{4b}$ | $X^5/X^6$ | $Y^{1a}-Y^{3b}$ | $Y^{4a}-Y^{18b}$ | R |
|---|---|---|---|---|---|---|---|---|
| 108 | D | H | H | H | H | H | H | $CH_3$ |
| 109 | H | D | H | H | H | H | H | $CH_3$ |
| 110 | H | H | D | H | H | H | H | $CH_3$ |
| 111 | H | H | H | D | H | H | H | $CH_3$ |
| 112 | H | H | H | H | D | H | H | $CH_3$ |
| 113 | D | D | H | H | H | H | H | $CH_3$ |
| 114 | D | H | D | H | H | H | H | $CH_3$ |
| 115 | D | H | H | D | H | H | H | $CH_3$ |
| 116 | D | H | H | H | D | H | H | $CH_3$ |
| 117 | D | H | H | H | H | D | H | $CH_3$ |
| 118 | D | H | H | H | H | H | D | $CH_3$ |
| 119 | D | H | H | H | H | H | H | $CD_3$ |
| 120 | H | D | D | H | H | H | H | $CH_3$ |
| 121 | H | D | H | D | H | H | H | $CH_3$ |
| 122 | H | D | H | H | D | H | H | $CH_3$ |
| 123 | H | D | H | H | H | D | H | $CH_3$ |
| 124 | H | D | H | H | H | H | D | $CH_3$ |
| 125 | H | D | H | H | H | H | H | $CD_3$ |
| 126 | H | H | D | D | H | H | H | $CH_3$ |
| 127 | H | H | D | H | D | H | H | $CH_3$ |
| 128 | H | H | D | H | H | D | H | $CH_3$ |
| 129 | H | H | D | H | H | H | D | $CH_3$ |
| 130 | H | H | D | H | H | H | H | $CD_3$ |
| 131 | H | H | H | D | D | H | H | $CH_3$ |
| 132 | H | H | H | D | H | D | H | $CH_3$ |
| 133 | H | H | H | D | H | H | D | $CH_3$ |
| 134 | H | H | H | D | H | H | H | $CD_3$ |
| 135 | H | H | H | H | D | D | H | $CH_3$ |
| 136 | H | H | H | H | D | H | D | $CH_3$ |
| 137 | H | H | H | H | D | H | H | $CD_3$ |
| 138 | D | D | D | H | H | H | H | $CH_3$ |
| 139 | D | D | H | D | H | H | H | $CH_3$ |
| 140 | D | D | H | H | D | H | H | $CH_3$ |
| 141 | D | D | H | H | H | D | H | $CH_3$ |
| 142 | D | D | H | H | H | H | D | $CH_3$ |
| 143 | D | D | H | H | H | H | H | $CD_3$ |
| 144 | D | H | D | D | H | H | H | $CH_3$ |
| 145 | D | H | D | H | D | H | H | $CH_3$ |
| 146 | D | H | D | H | H | D | H | $CH_3$ |
| 147 | D | H | D | H | H | H | D | $CH_3$ |
| 148 | D | H | D | H | H | H | H | $CD_3$ |
| 149 | D | H | H | D | D | H | H | $CH_3$ |
| 150 | D | H | H | D | H | D | H | $CH_3$ |
| 151 | D | H | H | D | H | H | D | $CH_3$ |
| 152 | D | H | H | D | H | H | H | $CD_3$ |
| 153 | D | H | H | H | D | D | H | $CH_3$ |
| 154 | D | H | H | H | D | H | D | $CH_3$ |
| 155 | D | H | H | H | D | H | H | $CD_3$ |
| 156 | D | H | H | H | H | D | D | $CH_3$ |
| 157 | D | H | H | H | H | D | H | $CD_3$ |
| 158 | D | H | H | H | H | H | D | $CD_3$ |
| 159 | H | D | D | D | H | H | H | $CH_3$ |
| 160 | H | D | D | H | D | H | H | $CH_3$ |
| 161 | H | D | D | H | H | D | H | $CH_3$ |
| 162 | H | D | D | H | H | H | D | $CH_3$ |
| 163 | H | D | D | H | H | H | H | $CD_3$ |
| 164 | H | D | H | D | D | H | H | $CH_3$ |
| 165 | H | D | H | D | H | D | H | $CH_3$ |
| 166 | H | D | H | D | H | H | D | $CH_3$ |
| 167 | H | D | H | D | H | H | H | $CD_3$ |
| 168 | H | D | H | H | D | D | H | $CH_3$ |
| 169 | H | D | H | H | D | H | D | $CH_3$ |
| 170 | H | D | H | H | D | H | H | $CD_3$ |
| 171 | H | D | H | H | H | D | D | $CH_3$ |
| 172 | H | D | H | H | H | D | H | $CD_3$ |
| 173 | H | D | H | H | H | H | D | $CD_3$ |
| 174 | H | H | D | D | D | H | H | $CH_3$ |
| 175 | H | H | D | D | H | D | H | $CH_3$ |
| 176 | H | H | D | D | H | H | D | $CH_3$ |
| 177 | H | H | D | D | H | H | H | $CD_3$ |
| 178 | H | H | D | H | D | D | H | $CH_3$ |
| 179 | H | H | D | H | D | H | D | $CH_3$ |
| 180 | H | H | D | H | D | H | H | $CD_3$ |
| 181 | H | H | D | H | H | D | D | $CH_3$ |
| 182 | H | H | D | H | H | D | H | $CD_3$ |
| 183 | H | H | D | H | H | H | D | $CD_3$ |
| 184 | H | H | H | D | D | D | H | $CH_3$ |
| 185 | H | H | H | D | D | H | D | $CH_3$ |
| 186 | H | H | H | D | D | H | H | $CD_3$ |
| 187 | H | H | H | D | H | D | D | $CH_3$ |
| 188 | H | H | H | D | H | D | H | $CD_3$ |
| 189 | H | H | H | D | H | H | D | $CD_3$ |
| 190 | H | H | H | H | D | D | D | $CH_3$ |
| 191 | H | H | H | H | D | D | H | $CD_3$ |
| 192 | H | H | H | H | D | H | D | $CD_3$ |
| 193 | D | D | D | D | H | H | H | $CH_3$ |
| 194 | D | D | D | H | D | H | H | $CH_3$ |
| 195 | D | D | D | H | H | D | H | $CH_3$ |
| 196 | D | D | D | H | H | H | D | $CH_3$ |
| 197 | D | D | D | H | H | H | H | $CD_3$ |
| 198 | D | D | H | D | D | H | H | $CH_3$ |
| 199 | D | D | H | D | H | D | H | $CH_3$ |
| 200 | D | D | H | D | H | H | D | $CH_3$ |
| 201 | D | D | H | D | H | H | H | $CD_3$ |
| 202 | D | D | H | H | D | D | H | $CH_3$ |
| 203 | D | D | H | H | D | H | D | $CH_3$ |
| 204 | D | D | H | H | D | H | H | $CD_3$ |
| 205 | D | D | H | H | H | D | D | $CH_3$ |
| 206 | D | D | H | H | H | D | H | $CD_3$ |
| 207 | D | D | H | H | H | H | D | $CD_3$ |
| 208 | D | H | D | D | D | H | H | $CH_3$ |
| 209 | D | H | D | D | H | D | H | $CH_3$ |
| 210 | D | H | D | D | H | H | D | $CH_3$ |
| 211 | D | H | D | D | H | H | H | $CD_3$ |
| 212 | D | H | D | H | D | D | H | $CH_3$ |
| 213 | D | H | D | H | D | H | D | $CH_3$ |
| 214 | D | H | D | H | D | H | H | $CD_3$ |
| 215 | D | H | D | H | H | D | D | $CH_3$ |
| 216 | D | H | D | H | H | D | H | $CD_3$ |
| 217 | D | H | D | H | H | H | D | $CD_3$ |
| 218 | D | H | H | D | D | D | H | $CH_3$ |
| 219 | D | H | H | D | D | H | D | $CH_3$ |
| 220 | D | H | H | D | D | H | H | $CD_3$ |
| 221 | D | H | H | D | H | D | D | $CH_3$ |
| 222 | D | H | H | D | H | D | H | $CD_3$ |
| 223 | D | H | H | D | H | H | D | $CD_3$ |
| 224 | D | H | H | H | D | D | D | $CH_3$ |
| 225 | D | H | H | H | D | D | H | $CD_3$ |
| 226 | D | H | H | H | D | H | D | $CD_3$ |
| 227 | D | H | H | H | H | D | D | $CD_3$ |
| 228 | H | D | D | D | D | H | H | $CH_3$ |
| 229 | H | D | D | D | H | D | H | $CH_3$ |
| 230 | H | D | D | D | H | H | D | $CH_3$ |
| 231 | H | D | D | D | H | H | H | $CD_3$ |
| 232 | H | D | D | H | D | D | H | $CH_3$ |
| 233 | H | D | D | H | D | H | D | $CH_3$ |
| 234 | H | D | D | H | D | H | H | $CD_3$ |
| 235 | H | D | D | H | H | D | D | $CH_3$ |

TABLE 1-continued

Exemplary Embodiments of Formula I

| Compound # | $X^{1a}/X^{1b}$ | $X^{2a}/X^{2b}$ | $X^3$ | $X^{4a}/X^{4b}$ | $X^5/X^6$ | $Y^{1a}-Y^{3b}$ | $Y^{4a}-Y^{18b}$ | R |
|---|---|---|---|---|---|---|---|---|
| 236 | H | D | D | H | H | D | H | $CD_3$ |
| 237 | H | D | D | H | H | H | D | $CD_3$ |
| 238 | H | D | D | H | D | D | H | $CH_3$ |
| 239 | H | D | H | D | D | H | D | $CH_3$ |
| 240 | H | D | H | D | D | H | H | $CD_3$ |
| 241 | H | D | H | D | H | D | D | $CH_3$ |
| 242 | H | D | H | D | H | D | H | $CD_3$ |
| 243 | H | D | H | D | H | H | D | $CD_3$ |
| 244 | H | D | H | H | D | D | D | $CH_3$ |
| 245 | H | D | H | H | D | D | H | $CD_3$ |
| 246 | H | D | H | H | D | H | D | $CD_3$ |
| 247 | H | D | H | H | H | D | D | $CD_3$ |
| 248 | H | H | D | D | D | D | H | $CH_3$ |
| 249 | H | H | D | D | D | H | D | $CH_3$ |
| 250 | H | H | D | D | D | H | H | $CD_3$ |
| 251 | H | H | D | D | H | D | D | $CH_3$ |
| 252 | H | H | D | D | H | D | H | $CD_3$ |
| 253 | H | H | D | D | H | H | D | $CD_3$ |
| 254 | H | H | D | H | D | D | D | $CH_3$ |
| 255 | H | H | D | H | D | D | H | $CD_3$ |
| 256 | H | H | D | H | D | H | D | $CD_3$ |
| 257 | H | H | D | H | H | D | D | $CD_3$ |
| 258 | H | H | H | D | D | D | D | $CH_3$ |
| 259 | H | H | H | D | D | D | H | $CD_3$ |
| 260 | H | H | H | D | D | H | D | $CD_3$ |
| 261 | H | H | H | D | H | D | D | $CD_3$ |
| 262 | H | H | H | H | D | D | D | $CD_3$ |
| 263 | D | D | D | D | D | H | D | $CH_3$ |
| 264 | D | D | D | D | D | H | H | $CH_3$ |
| 265 | D | D | D | D | H | H | D | $CH_3$ |
| 266 | D | D | D | D | H | H | H | $CD_3$ |
| 267 | D | D | D | H | D | D | H | $CH_3$ |
| 268 | D | D | D | H | D | H | H | $CH_3$ |
| 269 | D | D | D | H | H | D | H | $CD_3$ |
| 270 | D | D | H | D | H | D | D | $CH_3$ |
| 271 | D | D | H | D | H | D | H | $CD_3$ |
| 272 | D | D | H | D | H | H | D | $CD_3$ |
| 273 | D | D | H | D | D | D | H | $CH_3$ |
| 274 | D | D | H | D | D | H | D | $CH_3$ |
| 275 | D | D | H | D | D | H | H | $CD_3$ |
| 276 | D | D | H | D | H | D | D | $CH_3$ |
| 277 | D | D | H | D | H | D | H | $CD_3$ |
| 278 | D | D | H | D | H | H | D | $CD_3$ |
| 279 | D | D | H | H | D | D | D | $CH_3$ |
| 280 | D | D | H | H | D | D | H | $CD_3$ |
| 281 | D | D | H | H | D | H | D | $CD_3$ |
| 282 | D | D | H | H | H | D | D | $CD_3$ |
| 283 | D | H | D | D | D | D | H | $CH_3$ |
| 284 | D | H | D | D | D | H | D | $CH_3$ |
| 285 | D | H | D | D | D | H | H | $CD_3$ |
| 286 | D | H | D | D | H | D | D | $CH_3$ |
| 287 | D | H | D | D | H | D | H | $CD_3$ |
| 288 | D | H | D | D | H | H | D | $CD_3$ |
| 289 | D | H | D | H | D | D | D | $CH_3$ |
| 290 | D | H | D | H | D | D | H | $CD_3$ |
| 291 | D | H | D | H | D | H | D | $CD_3$ |
| 292 | D | H | D | H | H | D | D | $CD_3$ |
| 293 | D | H | H | D | D | D | D | $CH_3$ |
| 294 | D | H | H | D | D | D | H | $CD_3$ |
| 295 | D | H | H | D | D | H | D | $CD_3$ |
| 296 | D | H | H | D | H | D | D | $CD_3$ |
| 297 | D | H | H | H | D | D | D | $CD_3$ |
| 298 | H | D | D | D | D | D | H | $CH_3$ |
| 299 | H | D | D | D | D | H | D | $CH_3$ |
| 300 | H | D | D | D | D | H | H | $CD_3$ |
| 301 | H | D | D | D | H | D | D | $CH_3$ |
| 302 | H | D | D | D | H | D | H | $CD_3$ |
| 303 | H | D | D | D | H | H | D | $CD_3$ |
| 304 | H | D | D | H | D | D | D | $CH_3$ |
| 305 | H | D | D | H | D | D | H | $CD_3$ |
| 306 | H | D | D | H | D | H | D | $CD_3$ |
| 307 | H | D | D | H | H | D | D | $CD_3$ |
| 308 | H | D | H | D | D | D | D | $CH_3$ |
| 309 | H | D | H | D | D | D | H | $CD_3$ |
| 310 | H | D | H | D | D | H | D | $CD_3$ |
| 311 | H | D | H | D | H | D | D | $CD_3$ |
| 312 | H | D | H | H | D | D | D | $CD_3$ |
| 313 | H | H | D | D | D | D | D | $CH_3$ |
| 314 | H | H | D | D | D | D | H | $CD_3$ |
| 315 | H | H | D | D | D | H | D | $CD_3$ |
| 316 | H | H | D | D | H | D | D | $CD_3$ |
| 317 | H | H | D | H | D | D | D | $CD_3$ |
| 318 | H | H | H | D | D | D | D | $CD_3$ |
| 319 | D | D | D | D | D | D | H | $CH_3$ |
| 320 | D | D | D | D | D | H | D | $CH_3$ |
| 321 | D | D | D | D | D | H | H | $CD_3$ |
| 322 | D | D | D | D | H | D | D | $CH_3$ |
| 323 | D | D | D | D | H | D | H | $CD_3$ |
| 324 | D | D | D | D | H | H | D | $CD_3$ |
| 325 | D | D | D | H | D | D | D | $CH_3$ |
| 326 | D | D | D | H | D | D | H | $CD_3$ |
| 327 | D | D | D | H | D | H | D | $CD_3$ |
| 328 | D | D | D | H | H | D | D | $CD_3$ |
| 329 | D | D | H | D | D | D | D | $CH_3$ |
| 330 | D | D | H | D | D | D | H | $CD_3$ |
| 331 | D | D | H | D | D | H | D | $CD_3$ |
| 332 | D | D | H | D | H | D | D | $CD_3$ |
| 333 | D | D | H | H | D | D | D | $CD_3$ |
| 334 | D | H | D | D | D | D | D | $CH_3$ |
| 335 | D | H | D | D | D | D | H | $CD_3$ |
| 336 | D | H | D | D | D | H | D | $CD_3$ |
| 337 | D | H | D | D | H | D | D | $CD_3$ |
| 338 | D | H | D | H | D | D | D | $CD_3$ |
| 339 | D | H | H | D | D | D | D | $CD_3$ |
| 340 | H | D | D | D | D | D | D | $CH_3$ |
| 341 | H | D | D | D | D | D | H | $CD_3$ |
| 342 | H | D | D | D | D | H | D | $CD_3$ |
| 343 | H | D | D | D | H | D | D | $CD_3$ |
| 344 | H | D | D | H | D | D | D | $CD_3$ |
| 345 | H | D | H | D | D | D | D | $CD_3$ |
| 346 | H | H | D | D | D | D | D | $CD_3$ |
| 347 | D | D | D | D | D | D | D | $CH_3$ |
| 348 | D | D | D | D | D | D | H | $CD_3$ |
| 349 | D | D | D | D | D | H | D | $CD_3$ |
| 350 | D | D | D | D | H | D | D | $CD_3$ |
| 351 | D | D | D | H | D | D | D | $CD_3$ |
| 352 | D | D | H | D | D | D | D | $CD_3$ |
| 353 | D | H | D | D | D | D | D | $CD_3$ |
| 354 | H | D | D | D | D | D | D | $CD_3$ |
| 355 | D | D | D | D | D | D | D | $CD_3$ | or a pharmaceutically acceptable salt thereof.

In some embodiments of Formula I, each of $X^{1a}$, $X^{1b}$, $X^{2a}$, $X^{2b}$, $X^3$, $X^{4a}$, $X^{4b}$, $X^5$, and $X^6$ is hydrogen; and the compound is a compound of Formula II:

(II)

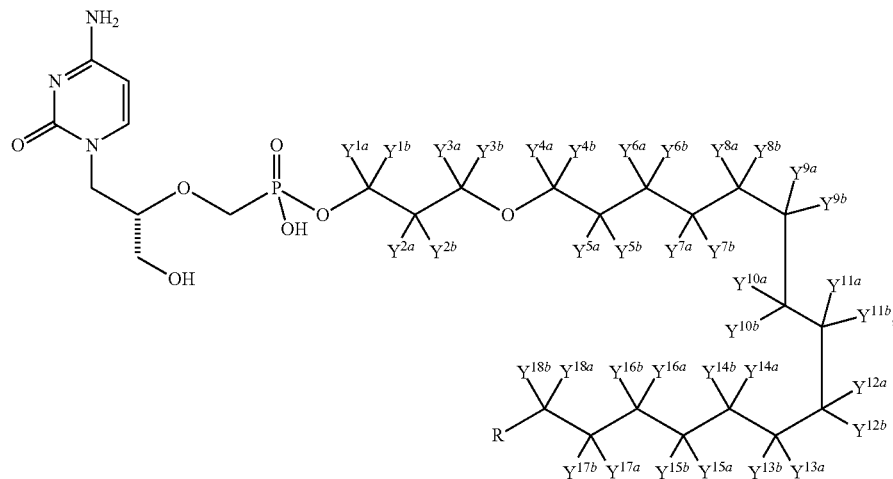

wherein $Y^{1a}$, $Y^{1b}$, $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$ are each independently selected from hydrogen and deuterium; and R is selected from $CH_3$, $CH_2D$, $CHD_2$, and $CD_3$;

provided that when $Y^{1a}$, $Y^{1b}$, $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$ are all hydrogen, then R comprises at least one deuterium.

In certain embodiments of Formula II, R is selected from $CH_3$, and $CD_3$. In some aspects of these embodiments, R is $CD_3$. In other aspects of these embodiments, R is $CH_3$.

Embodiments of Formula II relating to one or more of $Y^{1a}$, $Y^{1b}$, $Y^{2a}$, $Y^{2b}$, $Y^{3a}$, $Y^{3b}$, $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$ and specific aspects thereof are the same as those set forth above for Formula I.

In one embodiment of Formula II, $Y^{1a}$, $Y^{1b}$, $Y^{2a}$, $Y^{2b}$, $Y^{3a}$, and $Y^{3b}$ are all the same; $Y^{4a}$, $Y^{4b}$, $Y^{5a}$, $Y^{5b}$, $Y^{6a}$, $Y^{6b}$, $Y^{7a}$, $Y^{7b}$, $Y^{8a}$, $Y^{8b}$, $Y^{9a}$, $Y^{9b}$, $Y^{10a}$, $Y^{10b}$, $Y^{11a}$, $Y^{11b}$, $Y^{12a}$, $Y^{12b}$, $Y^{13a}$, $Y^{13b}$, $Y^{14a}$, $Y^{14b}$, $Y^{15a}$, $Y^{15b}$, $Y^{16a}$, $Y^{16b}$, $Y^{17a}$, $Y^{17b}$, $Y^{18a}$, and $Y^{18b}$ are all the same, and the compound is selected from any one of the compounds set forth in Table 2 (below):

TABLE 2

Exemplary Embodiments of Formula II

| Compound | $Y^{1a}$-$Y^{3b}$ | $Y^{4a}$-$Y^{18b}$ | R |
|---|---|---|---|
| 101 | D | H | $CH_3$ |
| 102 | H | D | $CH_3$ |
| 103 | D | D | $CH_3$ |
| 104 | H | H | $CD_3$ |
| 105 | H | D | $CD_3$ |
| 106 | D | H | $CD_3$ |
| 107 | D | D | $CD_3$ | or a pharmaceutically acceptable salt thereof.

In another set of embodiments, any atom not designated as deuterium in any of the embodiments set forth above is present at its natural isotopic abundance.

The synthesis of compounds of Formula I may be prepared by one skilled in the art in a manner analogous to the methods described in the following sources, using appropriately deuterated starting materials and reagents. Relevant procedures analogous to those of use for the preparation of compounds of Formula I and intermediates thereof are disclosed, for instance in PCT WO 2012031045; WO 2011053812; WO 2006110655; and WO 2005087788; in the publications Viruses (2010), 2, 2213-2225; and Antimicrobial Agents and Chemotherapy (2002), 46(4), 991-995; and in United States patent publication US20120058976.

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

Exemplary Synthesis

A convenient method for synthesizing compounds of Formula A is depicted in Scheme 1 below.

Scheme 1: General Synthesis of Compounds of Formula A, wherein R¹ is not Hydrogen (Formula I).
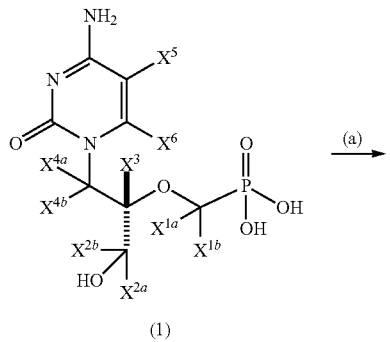
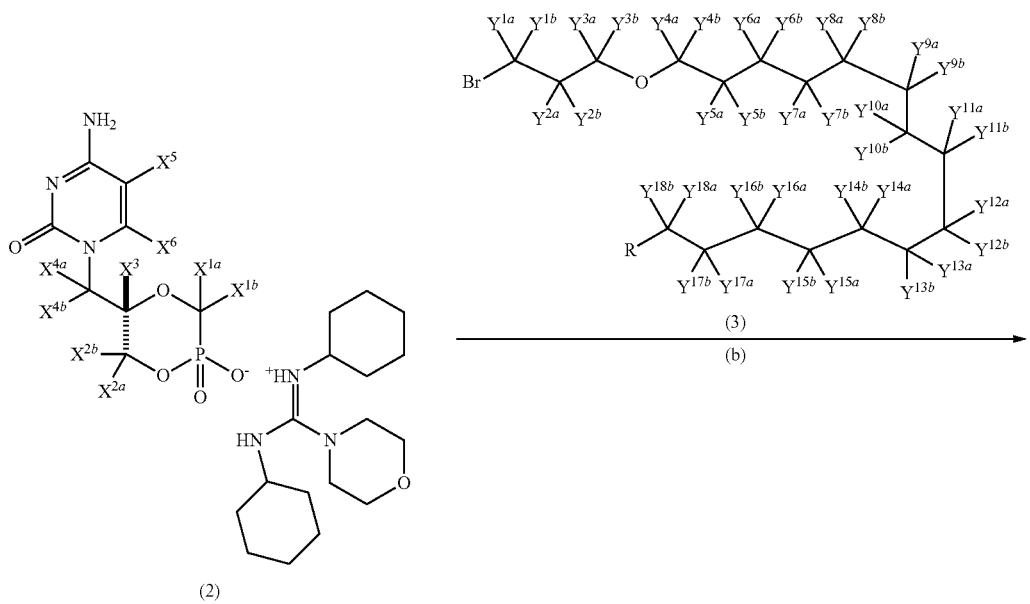
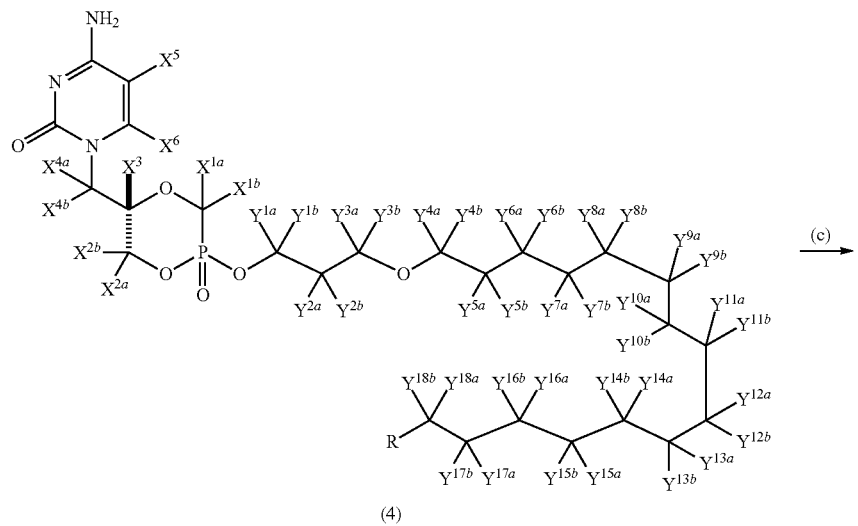

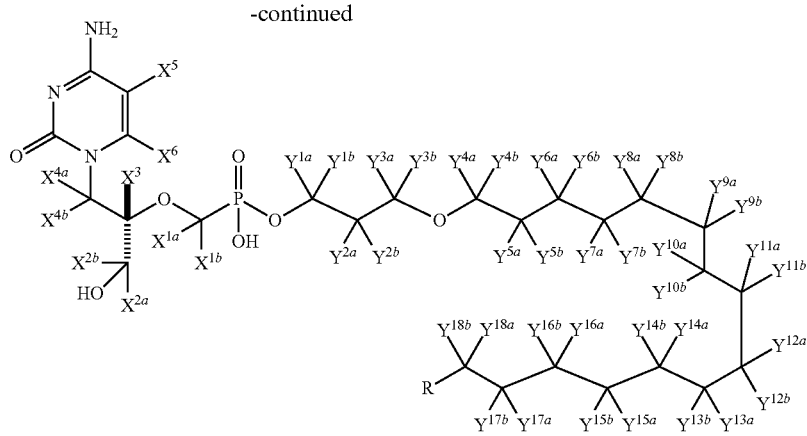

Formula 1

Reagents and conditions: (a) DCC, Pyridine, N,N-dicyclohexyl-4-morpholine-carboxamidine (DCMC); (b) heat; (c) NaOH, H$_2$O In a manner analogous to a procedure described in US 20120058976, appropriately deuterated acyl nucleotide, cidofovir intermediate (1; Formula A, wherein R$^1$ is hydrogen) is cyclized with a dehydrating reagent such as DCC in the presence of DCMC to produce appropriately deuterated cyclic phosphonate DCMC salt intermediate (2) using pyridine as a base, and at elevated temperature. Intermediate (2) is subsequently alkylated with appropriately deuterated bromopropyl intermediate (3) at elevated temperature producing appropriately deuterated cyclic phosphonate ester intermediate (4). Finally, ring opening of the cyclic phosphonate intermediate (4) using an aqueous base such as aqueous NaOH furnishes appropriately deuterated phosphonate compounds of Formula I.

Using commercially available reagents and deuterated reagents that can be readily prepared by known methods, compounds of Formula I can be prepared with greater than 90% or greater than 95% deuterium incorporation at each position designated as D (see below for details).

Appropriately deuterated compounds of Formula A, wherein R$^1$ is hydrogen are intermediates (1), for use in the preparation of compounds of Formula I according to Scheme 1. Such compounds may be prepared from corresponding deuterated reagents exemplified in Scheme 2 below.

Scheme 2: Preparation of a Compound of Formula A, wherein R$^1$ is Hydrogen (Intermediate (1).

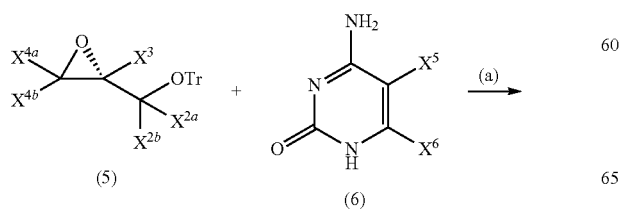

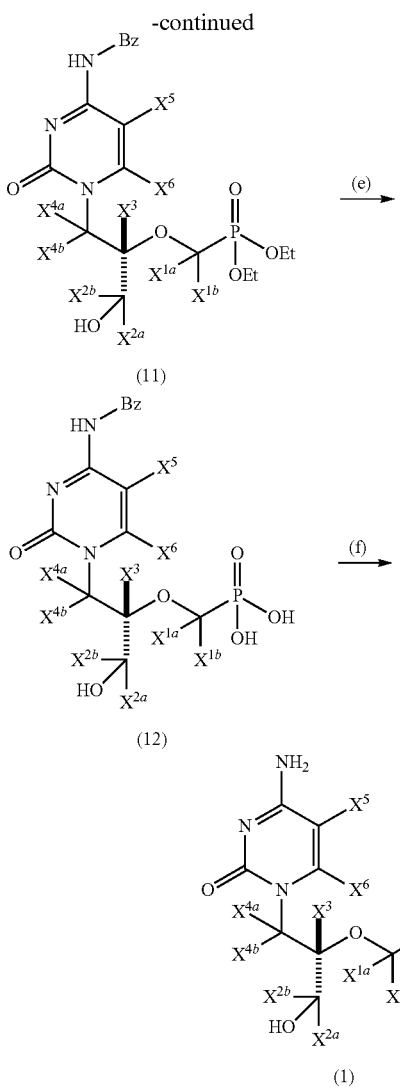

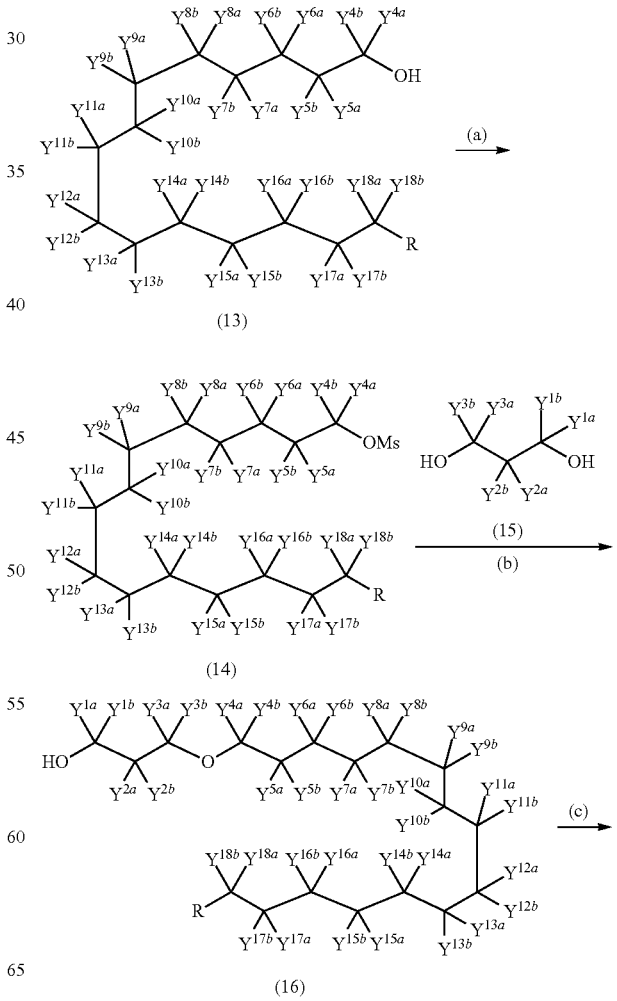

Reagents and conditions: (a) NaH; (b) (PhCO$_2$)$_2$; (c) NaH; (d) HCl; (e) TMS—Br; (f) conc. NH$_4$OH.

In a manner analogous to a procedure described by Brodfuehrer, P. et al., Tetrahedron Letters, 35(20), 3243-6; 1994, regiospecific ring opening of trityl protected and appropriately deuterated oxymethyoxirane intermediate (5) with appropriately deuterated cytosine intermediate (6) in the presence of catalytic amount of sodium hydride at elevated temperature, produces appropriately deuterated alkylated cytosine intermediate (7), which is subsequently treated with benzoic anhydride using a modified procedure described by McKenna, C. et al., Journal of Organometallic Chemistry, 690(10), 2673-2678; 2005, to furnish N-benzoyl protected and appropriately deuterated intermediate (8). Alkylation of intermediate (8) with appropriately deuterated diethyl tosyloxymethylphosphonate intermediate (9) in the presence of NaH produces appropriately deuterated nucleotide ester intermediate (10), which is subsequently detritylated by treating with gaseous HCl to afford the corresponding and appropriately deuterated alcohol intermediate (11). Deprotection of the ethyl ester of the phosphonate moiety of intermediate (11) with TMS-Br furnishes appropriately deuterated N-benzoyl protected phosphonic acid intermediate (12), which is finally treated with concentrated ammonium hydroxide to produce appropriately deuterated acyl nucleotide, cidofovir intermediate (1) (a compound of Formula A, wherein R$^1$ is hydrogen).

Cytosine-5,6-d$_2$ (98 atom % D) intermediate (6a) is commercially available. Cytosine-5,-d, (6b), and Cytosine-6,-d (6c), are prepared according to a procedure described by Kiritani, R. et. al., Journal of Labelled Compounds and Radiopharmaceuticals, 23(2), 207-14; 1986.

Use of appropriately deuterated reagents allows deuterium incorporation at the $X^{1a, 1b}$, $X^{2a, 2b}$, $X^3$, $X^{4a, 4b}$, $X^5$ and $X^6$ positions of a compound of Formula I, or any appropriate intermediate herein, e.g., 90, 95, 97, or 99% deuterium incorporation at any $X^{1a, 1b}$, $X^{2a, 2b}$, $X^{4a, 4b}$, $X^5$ and/or $X^6$.

Using commercially available reagents and deuterated reagents that can be readily prepared by known methods, compounds of Formula A can be prepared with greater than 90% or greater than 95% deuterium incorporation at each position designated as D (see below for details).

Appropriately deuterated intermediate (3), for use in the preparation of compounds of Formula I according to Scheme 1 may be prepared from corresponding deuterated reagents exemplified in Scheme 3 below.

Scheme 3: Preparation of Intermediate (3)

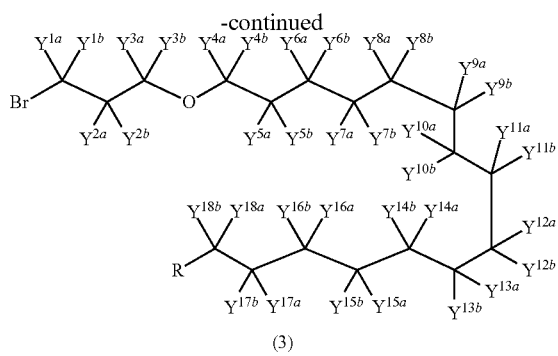

(3)

Reagents and conditions: (a) CH$_3$SO$_2$Cl, DIEA; (b) NaH; (c) CBr$_4$, Ph$_3$P In a manner analogous to a procedure described in US 20120058976, appropriately deuterated hexadecanol intermediate (13) is treated with methanesulfonyl chloride in the presence of a base such as diisopropylethylamine to produce appropriately deuterated mesylate intermediate (14), which is subsequently treated with appropriately deuterated diol intermediate (15) in the presence of a suitable base such as metal hydride (e.g. sodium hydride) affording appropriately deuterated alcohol intermediate (16). Finally, intermediate (16) is treated with triphenylphosphine and carbon tetrabromide to furnish appropriately deuterated bromopropyl intermediate (3).

The following intermediates (13) are commercially available: 1-Hexadecan-d$_{33}$-ol (98 atom % D) (13a), n-Hexadecyl-d$_{31}$ alcohol (98 atom % D) (13b), n-Hexadecyl-16,16,16-d$_3$ alcohol (99 atom % D) (13c), n-Hexadecyl-15,15,16,16,16-d$_5$ alcohol (98 atom % D) (13d), n-Hexadecyl-2,2,16,16,16-d$_5$ alcohol (98 atom % D) (13e), n-Hexadecyl-1,1,2,2-d$_4$ alcohol (99 atom % D) (13f). The following intermediates (13) are prepared according to the published procedures: 1-Hexadecan-1,1-d$_2$-ol (13g), Elliger, C., Journal of Labelled Compounds and Radiopharmaceuticals, 20(1), 135-41; 1983; l-Hexadecan-2,2-d$_2$-ol (13h), Matsumori, N. et al., Biochemistry, 51(42), 8363-8370; 2012; 1-Hexadecan-1,1,10,10-d$_4$-ol (13i), Hoskovec, M. et al., Tetrahedron, 58(45), 9193-9201; 2002; 1-Hexadecan-13,13,14,14-d$_4$-ol (13j), Horner, J. et al., Journal of Labelled Compounds and Radiopharmaceuticals, 55(11), 406-410; 2012. 1-Hexadecan-8,8,9,9,14,14-d$_6$-ol (13k) and 1-Hexadecan-8,8,9,9,13,13-d$_6$-ol (13l), are prepared according to a procedure described by Abad, J. et al., Journal of Organic Chemistry, 72(3), 760-764; 2007.

The following intermediates (15) are commercially available: 1,3-Propane-d$_6$-diol, (99 atom % D) or 1,3-Propane-diol-d$_8$ (98 atom % D) (15a); 1,3-Propane-2,2-d2 diol (98 atom % D) (15b). 1,3-Propanc-1,1,3,3-d$_4$-diol (15c) is prepared according to a procedure described by Dickschat, J. et al., European Journal of Organic Chemistry, 2011(18), 3339-3346; 2011.

Use of appropriately deuterated reagents allows deuterium incorporation at the Y$^{1a, 1b}$, Y$^{2a, 2b}$, Y$^{3a, 3b}$, Y$^{4a, 4b}$, Y$^{5a, 5b}$, Y$^{6a, 6b}$, Y$^{7a, 7b}$, Y$^{8a, 8b}$, Y$^{9a, 9b}$, Y$^{10a,10b}$, Y$^{11a, 11b}$, Y$^{12a, 12b}$, Y$^{13a, 13b}$, Y$^{14a, 14b}$, Y$^{15a, 15b}$, Y$^{16a, 16b}$, Y$^{17a, 17b}$, Y$^{18a, 18b}$ and R positions of a compound of Formula I, or any appropriate intermediate herein, e.g., 90, 95, 97, or 99% deuterium incorporation at any Y$^{1a, 1b}$, Y$^{2a, 2b}$, Y$^{3a, 3b}$, Y$^{4a, 4b}$, Y$^{5a, 5b}$, Y$^{6a, 6b}$, Y$^{7a, 7b}$, Y$^{8a, 8b}$, Y$^{9a, 9b}$, Y$^{10a,10b}$, Y$^{11a, 11b}$, Y$^{12a, 12b}$, Y$^{13a, 13b}$, Y$^{14a, 14b}$, Y$^{15a, 15b}$, Y$^{16a, 16b}$, Y$^{17a, 17b}$, Y$^{18a, 18b}$ and/or R.

Using commercially available reagents and deuterated reagents that can be readily prepared by known methods, compounds of Formula I can be prepared with greater than 90% or greater than 95% deuterium incorporation at each position designated as D (see below for details).

Appropriately deuterated intermediate (5), for use in the preparation of compounds of Formula A according to Scheme 2 may be prepared from corresponding deuterated reagents exemplified in Scheme 4 below.

Scheme 4: Preparation of Intermediate (5)

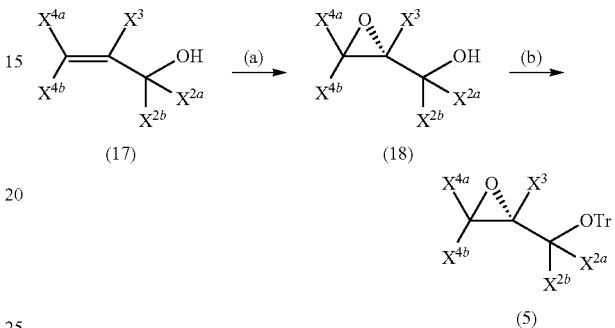

Reagents and conditions: (a) t-BuOOH, CSA-SBA-15catalyst, ambient; (b); Et$_3$N, DMAP, Trt-Cl In a manner analogous to procedure described by Selvaraj, M. et al., Microporous and Mesoporous Materials, 132(3), 494-500; 2010, epoxidation of appropriately deuterated ally alcohol intermediate (17) with t-butyl hydroperoxide at ambient reaction temperature furnishes appropriately deuterated (R)-glycidol intermediate (18), which is subsequently treated with trityl-chloride in the presence of a base such as trimethylamine, and catalytic amounts of DMAP in a manner analogous to a procedure described by Schweizer, E. et al., Synthesis 24, 3807-3814, 2007, producing trityl protected and appropriately deuterated oxymethyoxirane intermediate (5).

Allyl-d$_5$ alcohol (98 atom % D) (17a) is commercially available. The following intermediates (17) are prepared according to the published procedures: 2-Propen-2,3,3-d$_3$-1-ol (17b), Omichinski, J. et al., Journal of Labelled Compounds and Radiopharmaceuticals, 25(3), 263-75; 1988; 2-Propen-3,3-d$_2$-1-ol (17c), Sada, M. et al., Chemistry—A European Journal, 16(34), 10474-10481; 2010; 2-Propen-1,1-d$_2$-1-ol (17d), Krompiec, S. et al., Journal of Molecular Catalysis A: Chemical, 248(1-2), 198-209; 2006; 2-Propen-1,1,3,3-d$_4$-1-ol (17e), Deyerl, H. et al., Journal of Chemical Physics (1999), 110(3), 1450-1462; 2-Propen-1,1,2-d$_3$-1-ol (17f), Vasilatou, K. et al., Journal of Chemical Physics, 141(6), 064317/1-064317/13; 2014.

Use of appropriately deuterated reagents allows deuterium incorporation at the X$^{2a, 2b}$, X$^3$, and X$^{4a, 4b}$ positions of a compound of Formula I, or any appropriate intermediate herein, e.g., 90, 95, 97, or 99% deuterium incorporation at any X$^{2a, 2b}$, X$^3$, and/or X$^{4a, 4b}$.

Using commercially available reagents and deuterated reagents that can be readily prepared by known methods, compounds of Formula A can be prepared with greater than 90% or greater than 95% deuterium incorporation at each position designated as D (see below for details).

Appropriately deuterated intermediate (9), for use in the preparation of compounds of Formula A according to Scheme 2 may be prepared from corresponding deuterated reagents exemplified in Scheme 5 below.

Scheme 5: Preparation of Intermediate (9)

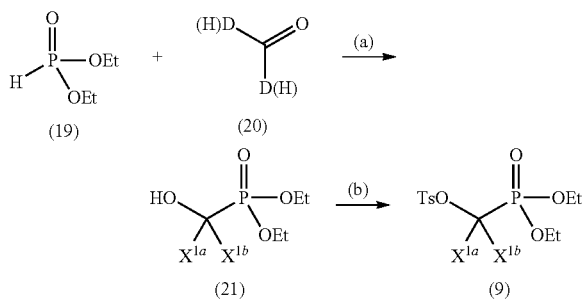

Reagents and conditions: (a) NaOH (b); p-Tosyl chloride, NaOH.

In a manner analogous to a procedure described in FR 2871466, hydrophosphonate intermediate (19) is hydroxymethylated with appropriately deuterated formaldehyde (20), in the presence of metal hydroxide, such as NaOH, at ambient temperature to afford appropriately deuterated hydroxymethylphosphonate intermediate (21), which is subsequently treated with tosyl chloride in the presence of metal hydroxide, such as NaOH, producing appropriately deuterated tosyl protected phoshonate intermediate (9).

Formalin-$d_2$ (98 atom % D) (20a) is commercially available, and formaldehyde-d (20b) is prepared according to a procedure described by Greenway, K. et al., Journal of Organic Chemistry (2012), 77(20), 9221-9226.

Use of appropriately deuterated reagents allows deuterium incorporation at the $X^{1a}$ and $X^{1b}$ positions of a compound of Formula A, or any appropriate intermediate herein, e.g., 90, 95, 97, or 99% deuterium incorporation at any $X^{1a}$ and/or $X^{1b}$.

Additional methods of synthesizing compounds of Formula I and their synthetic precursors, including those within routes not explicitly shown in schemes herein, are within the means of chemists of ordinary skill in the art. Synthetic chemistry transformations and protecting group methodologies (protection and deprotection) useful in synthesizing the applicable compounds are known in the art and include, for example, those described in Larock R, *Comprehensive Organic Transformations*, VCH Publishers (1989); Greene, T W et al., *Protective Groups in Organic Synthesis*, 3rd Ed., John Wiley and Sons (1999); Fieser, L et al., *Fieser and Fieser's Reagents for Organic Synthesis*, John Wiley and Sons (1994); and Paquette, L, ed., *Encyclopedia of Reagents for Organic Synthesis*, John Wiley and Sons (1995) and subsequent editions thereof.

Combinations of substituents and variables envisioned by this invention are only those that result in the formation of stable compounds.

Compositions

The invention also provides pharmaceutical compositions comprising an effective amount of a compound of Formula I (e.g., including any of the formulae herein), or a pharmaceutically acceptable salt of said compound; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, e.g.: Rabinowitz J D and Zaffaroni A C, U.S. Pat. No. 6,803,031, assigned to Alexza Molecular Delivery Corporation.

Topical administration of the pharmaceutical compositions of this invention is especially useful when the desired prevention and/or treatment involves areas or organs readily accessible by topical application. For topical application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of this invention may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the invention provides a method of coating an implantable medical device comprising the step of contacting said device with the coating composition described above. It will be obvious to those skilled in the art that the coating of the device will occur prior to implantation into a mammal.

According to another embodiment, the invention provides a method of impregnating an implantable drug release device comprising the step of contacting said drug release device with a compound or composition of this invention. Implantable drug release devices include, but are not limited to, biodegradable polymer capsules or bullets, non-degradable, diffusible polymer capsules and biodegradable polymer wafers.

According to another embodiment, the invention provides an implantable medical device coated with a compound or a composition comprising a compound of this invention, such that said compound is therapeutically active.

According to another embodiment, the invention provides an implantable drug release device impregnated with or containing a compound or a composition comprising a compound of this invention, such that said compound is released from said device and is therapeutically active.

Where an organ or tissue is accessible because of removal from the subject, such organ or tissue may be bathed in a medium containing a composition of this invention, a composition of this invention may be painted onto the organ, or a composition of this invention may be applied in any other convenient way.

In another embodiment, a composition of this invention further comprises a second therapeutic agent. The second therapeutic agent may be selected from any compound or therapeutic agent known to have or that demonstrates advantageous properties when administered with a compound having the same mechanism of action as brincidofovir. Such agents include those indicated as being useful in combination with brincidofovir, including but not limited to, those described in U.S. Pat. No. 8,642,577; and US patent applications 2013/0072458; 2012/0164104; and 2007/0003516.

Preferably, the second therapeutic agent is an agent useful in the prevention and/or treatment of a dsDNA viral infection selected from polyomavirus (including BK, John Cunningham virus (JCV), Merkel cell virus (MCV), KI polyomavirus (KIV), WU polyomavirus (WUV), Simian virus 40 (SV 40)), papillomavirus (including human papillomavirus, cottontail rabbit papillomavirus, equine papillomavirus and bovine papillomavirus), herpes virus including, but are not limited to, human herpes virus, such as Herpes simplex virus-1 (HSV-1), Herpes simplex virus-2 (HSV-2), human herpes virus 6 (HHV-6), varicella zoster virus (VZV), Epstein-Barr virus (EBV), lymphocryptovirus, cytomegalovirus (CMV) (including, but is not limited to, human cytomegalovirus (HCMV)), orthopoxvirus, smallpox, cowpox, camelpox, monkeypox, hepatitis B, hepatitis C virus, variola major and minor, vaccinia, human immunodeficiency virus (HIV), Ebola virus, papillomavirus, adenovirus, and polyomavirus, and a combination thereof; and a viral induced tumor selected from cervical cancer associated with papillomavirus, post transplant lymphoproliferative disorder (PTLD) associated with Epstein-Barr virus (EBV), brain cancer, colorectal cancer, nasopharyngeal carcinoma (NPC), Burkitt lymphoma (BL), lymphoma (e.g., B cell lymphoma, Hodgkin's lymphoma, Duncan's syndrome), Merkel cell carcinoma (MCC), prostate cancer, hepatocellular carcinoma, lung cancer, head and neck squamous cancers, prostate cancer, breast cancer, acute lymphocytic leukemia, adult acute myeloid leukemia, adult non Hodgkin's lymphoma, brain tumors, childhood cancers, childhood sarcoma, chronic lymphocytic leukemia, chronic myeloid leukemia, esophageal cancer, hairy cell leukemia, kidney cancer, liver cancer, multiple myeloma, neuroblastoma, oral cancer, pancreatic cancer, primary central nervous system lymphoma, skin cancer, and a combination thereof.

In one embodiment, the second therapeutic agent is selected from probenecid and carboplatin.

In another embodiment, the invention provides separate dosage forms of a compound of this invention and one or more of any of the above-described second therapeutic agents, wherein the compound and second therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, the compound of the present invention is present in an effective amount. As used herein, the term "effective amount" refers to an amount which, when administered in a proper dosing regimen, is sufficient to prevent and/or treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of a compound of this invention can range from about 50 mg to about 200 mg twice-weekly, about 5 mg to about 400 mg twice-weekly, about 0.5 mg to about 2000 mg twice-weekly, or about 0.005 mg to about 20 grams twice-weekly.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician. For example, guidance for selecting an effective dose can be determined by reference to the prescribing information for brincidofovir.

For pharmaceutical compositions that comprise a second therapeutic agent, an effective amount of the second therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these second therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety.

It is expected that some of the second therapeutic agents referenced above will act synergistically with the compounds of this invention. When this occurs, it will allow the effective dosage of the second therapeutic agent and/or the compound of this invention to be reduced from that required in a monotherapy. This has the advantage of minimizing toxic side effects of either the second therapeutic agent of a compound of this invention, synergistic improvements in efficacy, improved ease of administration or use and/or reduced overall expense of compound preparation or formulation.

Methods of Treatment

In another embodiment, the invention provides a method of modulating the activity of viral DNA polymerase in a cell, comprising contacting a cell with one or more compounds of Formula I herein, or a pharmaceutically acceptable salt thereof. In some embodiments, the method of modulating the activity of viral DNA polymerase in a cell is a method of inhibiting the activity of viral DNA polymerase.

According to another embodiment, the invention provides a method of preventing and/or treating a disease that is beneficially prevented and/or treated by brincidofovir in a subject in need thereof, comprising the step of administering to the subject an effective amount of a compound or a composition of this invention. In one embodiment the subject is a patient in need of such prevention and/or treatment. Such diseases are well known in the art and are disclosed in, but not limited to the following patents and published applications: WO 2012031045; WO 2011053812; WO 2006110655; and WO 2005087788. Such diseases include, but are not limited to, dsDNA viral infection selected from polyomavirus (including BK, John Cunningham virus (JCV), Merkel cell virus (MCV), KI polyomavirus (KIV), WU polyomavirus (WUV), Simian virus 40 (SV 40)), papillomavirus (including human papillomavirus, cottontail rabbit papillomavirus, equine papillomavirus and bovine papillomavirus), herpes virus including, but are not limited to, human herpes virus, such as Herpes simplex virus-1 (HSV-1), Herpes simplex virus-2 (HSV-2), human herpes virus 6 (HHV-6), varicella zoster virus (VZV), Epstein-Barr virus (EBV), lymphocryptovirus, cytomegalovirus (CMV) (including, but is not limited to, human cytomegalovirus (HCMV)), orthopoxvirus, smallpox, cowpox, camelpox, monkeypox, hepatitis B, hepatitis C virus, variola major and minor, vaccinia, human immunodeficiency virus (HIV), Ebola virus, papillomavirus, adenovirus, and polyomavirus, and a combination thereof; and a viral induced tumor selected from cervical cancer associated with papillomavirus, post transplant lymphoproliferative disorder (PTLD) associated with Epstein-Barr virus (EBV), brain cancer, colorectal cancer, nasopharyngeal carcinoma (NPC), Burkitt lymphoma (BL), lymphoma (e.g., B cell lymphoma, Hodgkin's lymphoma, Duncan's syndrome), Merkel cell carcinoma (MCC), prostate cancer, hepatocellular carcinoma, lung cancer, head and neck squamous cancers, prostate cancer, breast cancer, acute lymphocytic leukemia, adult acute myeloid leukemia, adult non-Hodgkin's lymphoma, brain tumors, childhood cancers, childhood sarcoma, chronic lymphocytic leukemia, chronic myeloid leukemia, esophageal cancer, hairy cell leukemia, kidney cancer, liver cancer, multiple myeloma, neuroblastoma, oral cancer, pancreatic cancer, primary central nervous system lymphoma, skin cancer, and a combination thereof.

In one particular embodiment, the method of this invention is used to prevent and/or treat a disease or condition selected from Ebola virus infection, cytomegalovirus infection, early versus late adenovirus infection, smallpox virus infection, and a serious or immediately life-threatening disease or condition caused by one or more of CMV, adenovirus, Herpes simplex virus, vaccinia, varicella zoster virus, and monkeypox virus for which no comparable or satisfactory alternative therapy is available in a subject in need thereof.

Identifying a subject in need of such prevention and/or treatment can be in the judgment of a subject or a health care professional and can be subjective (e.g. opinion) or objective (e.g. measurable by a test or diagnostic method).

In another embodiment, any of the above methods of prevention and/or treatment comprises the further step of co-administering to the subject in need thereof one or more second therapeutic agents. The choice of second therapeutic agent may be made from any second therapeutic agent known to be useful for co-administration with brincidofovir. The choice of second therapeutic agent is also dependent upon the particular disease or condition to be prevented and/or treated. Examples of second therapeutic agents that may be employed in the methods of this invention are those set forth above for use in combination compositions comprising a compound of this invention and a second therapeutic agent.

The term "co-administered" as used herein means that the second therapeutic agent may be administered together with a compound of this invention as part of a single dosage form (such as a composition of this invention comprising a compound of the invention and an second therapeutic agent as described above) or as separate, multiple dosage forms. Alternatively, the additional agent may be administered prior to, consecutively with, or following the administration of a compound of this invention. In such combination therapy treatment, both the compounds of this invention and the second therapeutic agent(s) are administered by conventional methods. The administration of a composition of this invention, comprising both a compound of the invention and a second therapeutic agent, to a subject does not preclude the separate administration of that same therapeutic agent, any other second therapeutic agent or any compound of this invention to said subject at another time during a course of treatment.

Effective amounts of these second therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the second therapeutic agent's optimal effective-amount range.

In one embodiment of the invention, where a second therapeutic agent is administered to a subject, the effective amount of the compound of this invention is less than its effective amount would be where the second therapeutic agent is not administered. In another embodiment, the effective amount of the second therapeutic agent is less than its effective amount would be where the compound of this invention is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of a compound of Formula I alone or together with one or more of the above-described second therapeutic agents in the manufacture of a medicament, either as a single composition or as separate dosage forms, for prevention and/or treatment in a subject of a disease, disorder or symptom set forth above. Another aspect of the invention is a compound of Formula I for use in the prevention and/or treatment in a subject of a disease, disorder or symptom thereof delineated herein.

Example X. Evaluation of Metabolic Stability Microsomal Assay:

Human liver microsomes (20 mg/mL) are obtained from Xenotech, LLC (Lenexa, Kans.). β-nicotinamide adenine dinucleotide phosphate, reduced form (NADPH), magnesium chloride (MgCk), and dimethyl sulfoxide (DMSO) are purchased from Sigma-Aldrich.

Determination of Metabolic Stability:

7.5 mM stock solutions of test compounds are prepared in DMSO. The 7.5 mM stock solutions are diluted to 12.5-50 µM in acetonitrile (ACN). The 20 mg/mL human liver microsomes are diluted to 0.625 mg/mL in 0.1 M potassium phosphate buffer, pH 7.4, containing 3 mM MgCk. The diluted microsomes are added to wells of a 96-well deep-well polypropylene plate in triplicate. A 10 µL aliquot of the 12.5-50 µM test compound is added to the microsomes and the mixture is pre-warmed for 10 minutes. Reactions are initiated by addition of pre-warmed NADPH solution. The final reaction volume is 0.5 mL and contains 0.5 mg/mL human liver microsomes, 0.25-1.0 µM test compound, and 2 mM NADPH in 0.1 M potassium phosphate buffer, pH 7.4, and 3 mM MgCk. The reaction mixtures are incubated at 37° C., and 50 µL aliquots are removed at 0, 5, 10, 20, and 30 minutes and added to shallow-well 96-well plates which contain 50 µL of ice-cold ACN with internal standard to stop the reactions. The plates are stored at 4° C. for 20 minutes after which 100 µL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the non-deuterated counterpart of the compound of Formula I and the positive control, 7-ethoxycoumarin (1 µM). Testing is done in triplicate.

Data Analysis:

The in vitro $t_{1/2}$s for test compounds are calculated from the slopes of the linear regression of % parent remaining (ln) vs incubation time relationship.

in vitro $t_{1/2}$=0.693/k k=−[slope of linear regression of % parent remaining (ln) vs incubation time]

Data analysis is performed using Microsoft Excel Software.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

I claim:

1. A compound of Formula (I):

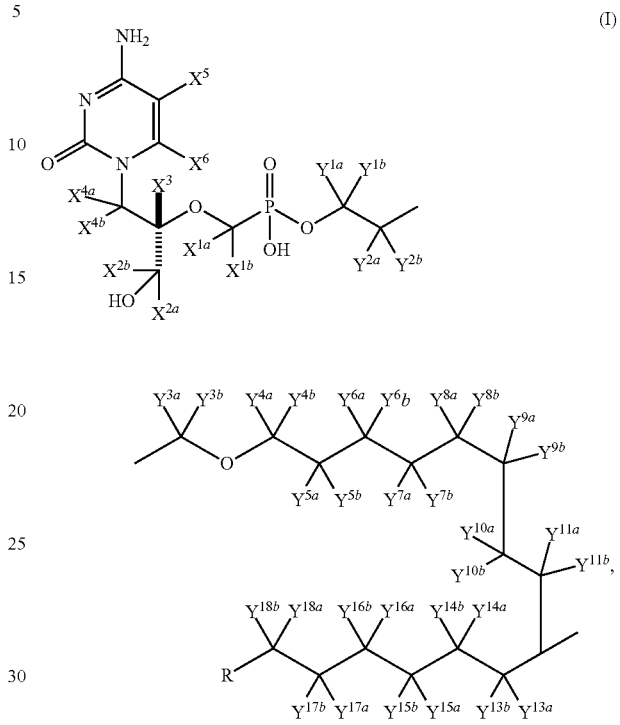

or a pharmaceutically acceptable salt thereof, wherein
$Y^{1a}, Y^{1b}, Y^{2a}, Y^{2b}, Y^{3a}$, and $Y^{3b}$ are each independently selected from hydrogen and deuterium;
$Y^{4a}, Y^{4b}, Y^{5a}, Y^{5b}, Y^{6a}, Y^{6b}, Y^{7a}, Y^{7b}, Y^{8a}, Y^{8b}, Y^{9a}, Y^{9b}, Y^{10a}, Y^{10b}, Y^{11a}, Y^{11b}, Y^{12a}, Y^{12b}, Y^{13a}, Y^{13b}, Y^{14a}, Y^{14b}, Y^{15a}, Y^{15b}, Y^{16a}, Y^{16b}, Y^{17a}, Y^{17b}, Y^{18a}$, and $Y^{18b}$ are each deuterium;
$X^{1a}, X^{1b}, X^{2a}, X^{2b}, X^3, X^{4a}, X^{4b}, X^5$, and $X^6$ are each independently selected from hydrogen and deuterium; and
R is $CD_3$,
wherein the deuterium incorporation at each designated deuterium atom is at least 50.1%.

2. The compound of claim 1, wherein $X^{1a}$ and $X^{1b}$ are the same.

3. The compound of claim 1, wherein $X^{2a}$ and $X^{2b}$ are the same.

4. The compound of claim 1, wherein $X^{4a}$ and $X^{4b}$ are the same.

5. The compound of claim 1, wherein $X^5$ and $X^6$ are the same.

6. The compound of claim 1, wherein, $X^{1a}$ and $X^{1b}$ are the same; $X^{2a}$ and $X^{2b}$ are the same; $X^{4a}$ and $X^{4b}$ are the same; and $X^5$ and $X^6$ are the same.

7. The compound of claim 1, wherein $Y^{1a}, Y^{1b}, Y^{2a}, Y^{2b}, Y^{3a}$ and $Y^{3b}$ are all the same.

8. The compound of claim 1, wherein each of $X^{1a}, X^{1b}, X^{2a}, X^{2b}, X^3, X^{4a}, X^{4b}, X^5$, and $X^6$ is hydrogen; and the compound is a compound of Formula II:

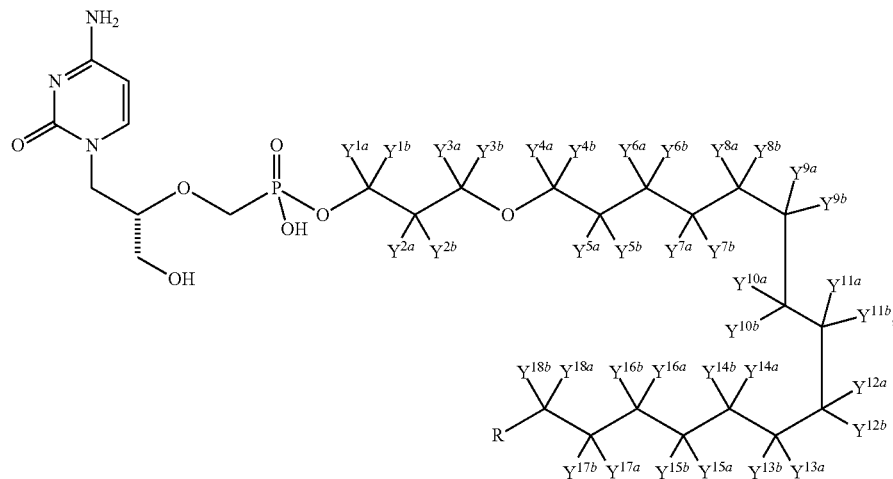

(II)

or a pharmaceutically acceptable salt thereof.

9. The compound of claim 1, wherein any atom not designated as deuterium is present at its natural isotopic abundance.

10. The compound of claim 8, wherein $Y^{1a}$, $Y^{1b}$, $Y^{2a}$, $Y^{2b}$, $Y^{3a}$ and $Y^{3b}$ are all the same; and the compound is selected from any one of the compounds in the table below:

| Compound | $Y^{1a}$-$Y^{3b}$ | $Y^{4a}$-$Y^{18b}$ | R |
|---|---|---|---|
| 105 | H | D | $CD_3$ |
| 107 | D | D | $CD_3$ | or a pharmaceutically acceptable salt thereof, wherein any atom not designated as deuterium is present at its natural isotopic abundance.

11. A pharmaceutical composition comprising a compound of claim 1 or a pharmaceutically acceptable salt thereof; and a pharmaceutically acceptable carrier.

12. A method of inhibiting the activity of viral DNA polymerase in a cell, comprising contacting the cell with a compound of claim 1, or a composition of claim 11.

13. A method of treating a dsDNA viral infection, comprising the step of administering to the subject in need thereof a compound of claim 1, or a composition of claim 11.

14. The method of claim 13, wherein the dsDNA viral infection is selected from Ebola virus infection, cytomegalovirus infection, adenovirus infection, smallpox virus infection, Herpes simplex virus infection, vaccinia infection, varicella zoster virus infection, and monkeypox virus infection.

15. The method of claim 14, comprising the additional step of co-administering a second therapeutic agent.

16. The compound of claim 1, wherein the deuterium incorporation at each designated deuterium atom is at least 90%.

17. The compound of claim 1, wherein the deuterium incorporation at each designated deuterium atom is at least 95%.

18. The compound of claim 1, wherein the deuterium incorporation at each designated deuterium atom is at least 97%.

19. The method of claim 15, wherein the second therapeutic agent is probenecid.

* * * * *